US008551426B2

(12) United States Patent
Kim et al.

(10) Patent No.: US 8,551,426 B2
(45) Date of Patent: Oct. 8, 2013

(54) COMPOUND FOR INHIBITING ACTIVITY OF RIBONUCLEASE, AND CONTAINER FOR STORING NUCLEIC ACID CONTAINING THE SAME

(75) Inventors: Jong Hoon Kim, Daejeon (KR); Hwangseo Park, Seoul (KR); Han Oh Park, Daejeon (KR)

(73) Assignee: Bioneer Corporation (KR)

( * ) Notice: Subject to any disclaimer, the term of this patent is extended or adjusted under 35 U.S.C. 154(b) by 0 days.

(21) Appl. No.: 13/377,377

(22) PCT Filed: Jun. 12, 2009

(86) PCT No.: PCT/KR2009/003179
§ 371 (c)(1),
(2), (4) Date: Dec. 13, 2011

(87) PCT Pub. No.: WO2010/143762
PCT Pub. Date: Dec. 16, 2010

(65) Prior Publication Data
US 2012/0114535 A1  May 10, 2012

(51) Int. Cl.
*B01L 3/00* (2006.01)
(52) U.S. Cl.
USPC ........ 422/549; 548/100; 548/125; 548/365.7; 546/1; 546/268.1; 546/112; 544/300; 435/199; 435/183
(58) Field of Classification Search
USPC ............ 422/549; 546/1, 268.1, 112; 435/183, 435/199
See application file for complete search history.

(56) References Cited

U.S. PATENT DOCUMENTS

| 4,272,595 A | 6/1981 | Webster et al. |
| 7,250,270 B2 | 7/2007 | Goldrick et al. |
| 2007/0032418 A1 | 2/2007 | Shapiro et al. |

FOREIGN PATENT DOCUMENTS

| EP | 1905762 | 4/2008 |
| KR | 10-2009-0107380 | 10/2009 |
| WO | 2006050034 | 5/2006 |
| WO | 2006095713 | 9/2006 |
| WO | 2008157680 | 12/2008 |
| WO | 2009/025159 | 2/2009 |
| WO | 2009023773 | 2/2009 |

OTHER PUBLICATIONS

Peter Blackburn, et al., "Ribonuclease Inhibitor from Human Placenta," The Journal of Biological Chemistry, Aug. 25, 1977, pp. 5904-5910, vol. 252, No. 16.
K. K. Reddi, et al., "Elevated serum ribonuclease in patients with pancreatic cancer," Proc. Natl. Acad. Sci. USA, Jul. 1976, pp. 2308-2310, vol. 73, No. 7.
Sambrook, et al., "7. Extraction, Purification, and Analysis of Messenger RNA from Eukaryotic Cells," Molecular Cloning, A Laboratory Manual, Second Edition, pp. 7.4-7.5.
F. Moreau, et al., Discovery of new Gram-negative antivirulence drugs: Structure and properties of novel *E. coli* WaaC inhibitors, Bioorganic & Medicinal Chemistry Letters 18, 2008, pp. 4022-4026.
European Search Report—European Application No. 09845856 issued on Sep. 19, 2012, citing WO2009/023773, WO2008/157680, EP1905762, WO2006/095713, Moreau et al. and WO2006/050034.

*Primary Examiner* — Monique Cole
(74) *Attorney, Agent, or Firm* — Cantor Colburn LLP

(57) ABSTRACT

Provided are an RNase activity inhibitory compound to effectively control the activity of the RNase promoting degradation of extracted RNAs and, in addition, a sample storage container including the same. The RNase activity inhibitory compound and the sample storage container according to the present invention may be effectively used to store RNAs during RNA extraction or the extracted RNAs.

8 Claims, 2 Drawing Sheets

COMPOUND FOR INHIBITING ACTIVITY OF RIBONUCLEASE, AND CONTAINER FOR STORING NUCLEIC ACID CONTAINING THE SAME

TECHNICAL FIELD

The present invention relates to a ribo-nuclease activity inhibitory compound that effectively controls activity of a ribo-nuclease which promotes degradation of ribonucleic acid ('RNA') and a sample storage container including the same, and more particularly, a process of extracting RNA from a living organism, a ribo-nuclease ('RNase') activity inhibitory compound, which is useful for storing the extracted RNA sample, and an RNA sample storage container including the same.

BACKGROUND ART

RNA is one kind of nucleic acids, has a different structure from deoxyribonucleic acid ('DNA') since it contains ribose instead of deoxyribose and, as a base, uracil instead of thymine. On the basis of structures and functions, the RNA may be classified into a ribosomal RNA (rRNA) to form a ribosome, a messenger RNA (mRNA) having genetic information for synthesis of a protein, which is transferred from DNA, and a transfer RNA (tRNA) to transfer an amino acid corresponding to a codon in the mRNA. Such RNAs may be degraded then synthesized again depending upon the uses and times and an RNase may participate in such processes.

Unlike a deoxyribo-nuclease ('DNase'), the RNase shows less controlled activity and incurs a problem of easy contamination at any time while collecting a sample until RNA extraction. Also, the RNase may act as a factor of decreasing yield and purity during isolation of pure RNA from a biological sample, therefore, activity thereof must be controlled.

An RNA is generally formed of a single strand and is easily degraded, compared to DNA. For diagnosis of Hepatitis C Virus ('HCV'), an RNA of the HCV ('HCV RNA') in a collected blood sample should be extracted before the HCV RNA is degraded by the RNase, followed by testing to determine the existence of HCV. In this case, if the HCV RNA has been degraded by the RNase in the blood, it may cause significant circumstances to determine a subject who is the owner of the blood sample as a non-infected person, even if he has been infected with the HCV.

Accordingly, it is significantly important to inhibit activity of RNase exposed during extraction of RNAs from a biological sample, however, the most important thing is that the sample is efficiently protected from being exposed to the RNase immediately after the storage of biological samples.

Meanwhile, in order to extract pure RNAs from blood, tissues of animal or plant, culture cells, or the like, two general methods include, for example, use of phenol and use of chaotropic salt.

Phenol well known in the art is a strong organic solvent used to dissolve components of a protein and/or cell, and may degrade the RNase just at the elution of the cells, before the RNase exhibits activity. Therefore, the above material may have an advantage of primarily preventing degradation of RNA. However, phenol also has a disadvantage as a harmful material to the human body and may significantly influence upon further processing if an organic solvent is not completely eliminated.

A chaotropic salt such as a guanidine salt possesses protein modification activity to modify RNase, thus inhibiting the activity of the RNase. The chaotropic salt may also function to attach the RNA to a silica surface, thus having an advantage of enabling easy isolation/purification of RNAs without using any organic solvent.

However, the foregoing methods are to control (inhibit) activity of RNases exposed during isolation of RNAs from a biological sample and, in the case where the RNAs have been already exposed to the RNases while storing the biological sample, cannot attain desired effects even though the activity of the RNases is inhibited during isolation of the RNAs.

An RNase inhibitory enzyme extracted from a human placenta is known to form a 1:1 composite with RNA and be used for non-competitive inhibition, thus being widely employed in the related art (see, Peter Blackburn et. al., JBC, 252:5904-5910 (1977)). If the above RNase inhibitory enzyme extracted from human placenta is treated using a sulfhydryl reagent such as p-hydroxymercury benzoate or N-ethyl maleimide in terms of enzyme features, the composite of RNase and RNase inhibitory enzyme is degraded and inactivated. In order to overcome such disadvantages, excess dithiothreitol ('DTT') must be used together with the above composite.

When an animal tissue specimen or the like is stored, a method of preventing degradation of a tissue fragment by RNase wherein the specimen is stored in a 50% or more alcoholic solution or, otherwise, in other solutions such as a polyethylene glycol (PEG) in order to prevent contact between the tissue fragment with moisture, has been reported. However, this method is restricted to experiments such as observation of tissue specimens in a staining process and considered to have limitations in universal or general use in the art (U.S. Pat. No. 7,250,270).

Vanadyl chloride may form a composite with RNase to exhibit effects of suppressing activities of degradation enzymes, however, also have a tendency of inhibiting action of an RNA polymerase. Accordingly, the above compound must be completely eliminated during extraction of the RNA, thus not being preferable (Sambrook et al., 1989).

Based on the foregoing description, currently available compounds for controlling activity of RNase may include: products using RNase inhibitory enzymes isolated from a human placenta as a main material; products containing at least 50% alcohol, which are useful for preventing degradation of RNAs by exposing a sample to alcohol instead of water; products having high concentration salts, which are useful for inhibiting the activity of RNase, or so forth. However, such products have limitation in the kinds of RNases, of which activities are efficiently inhibited by the products, in addition, may encounter a problem of requiring an alternative adjuvant and/or stabilizer added to prolong RNase activity inhibitory ability.

DISCLOSURE

Technical Problem

An object of the present invention is to provide an RNase activity inhibitory compound having strong activity inhibition against the RNase degrading RNAs. Another object of the present invention is to provide an RNA storage container including the RNase activity inhibitory compound according to the present invention, in order to stably store the RNA easily degraded while being exposed to the RNase during storage of a sample.

Technical Solution

In order to accomplish the foregoing purposes, the present invention provides an RNase activity inhibitory compound to effectively control (inhibit) activity of an RNase, which promotes degradation of an extracted RNA, wherein the compound may comprise compounds represented by the following Formulae 1 and 2:

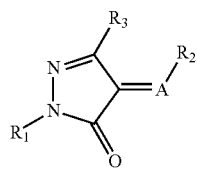

Formula 1

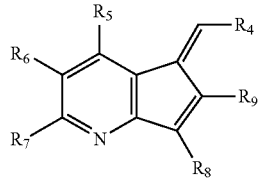

Formula 2

In Formula 1 or 2, A is CH or N; $R_1$ is a $(C_6\text{-}C_{20})$aryl or $(C_5\text{-}C_{15})$heteroaryl having 1 to 3 substituted or non-substituted $(C_1\text{-}C_7)$alkyl; $R_2$ or $R_4$ is each independently

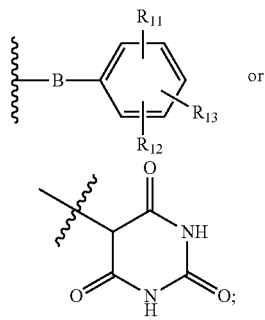

$R_3$ a linear or branched $(C_1\text{-}C_7)$alkyl; B in the substitute $R_2$ or $R_4$ is

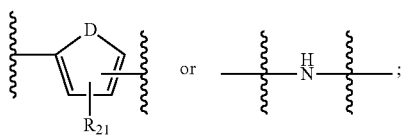

$R_5$ to $R_9$ are each independently hydrogen, linear or branched $(C_1\text{-}C_7)$alkyl, carboxylic acid, halogen atoms, cyano, amino, mono- or di$(C_1\text{-}C_7)$alkylamino, guanidine, urea or formyl; $R_{11}$, $R^{12}$ or $R_{13}$ is each independently hydrogen, linear or branched $(C_1\text{-}C_7)$alkyl, $(C_3\text{-}C_7)$cycloalkyl, $(C_3\text{-}C_{10})$cycloalkyl$(C_1\text{-}C_7)$alkyl, carboxylic acid, halogen atoms, cyano, nitro, amino, mono- or di$(C_1\text{-}C_7)$alkylamino, $(C_3\text{-}C_7)$cycloalkylamino, morpholine, morpholine oxide, piperazine, piperazine oxide, guanidine, urea, benzyl, benzyloxy or formyl; $R_{21}$ is hydrogen or linear or branched $(C_1\text{-}C_7)$alkyl; D is O, S or $-NR_{22}$; $R_{22}$ is hydrogen or $(C_1\text{-}C_7)$alkyl.

More particularly, the compounds represented by Formulae 1 and 2 may include compounds represented by any one of the following Formulae 3 to 6.

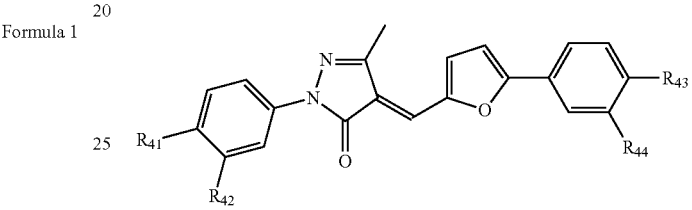

Formula 3

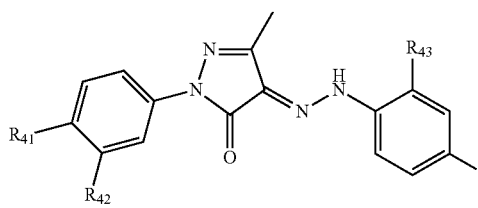

Formula 4

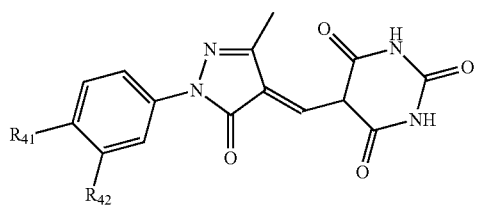

Formula 5

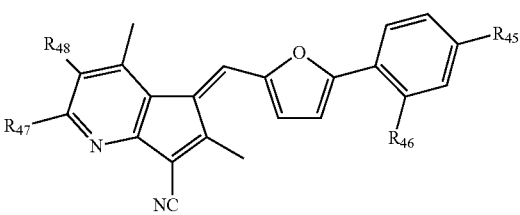

Formula 6

In Formulae 3 to 6, $R_{41}$ or $R_{42}$ is each independently hydrogen, methyl, ethyl, n-propyl or i-propyl; $R_{43}$ or $R_{44}$ is each independently hydrogen, methy, ethyl, n-propyl, propyl, carboxylic acid or nitro; $R_{45}$ or $R_{46}$ is each independently hydrogen, methyl, ethyl, n-propyl, i-propyl or carboxylic acid; $R_{47}$ or $R_{48}$ is each independently hydrogen, methyl, ethyl, cyano or amino.

The compound represented by Formula 5 may be present in an enol-keto form of tautomer.

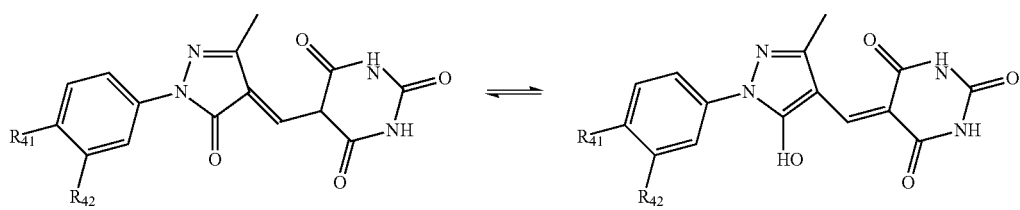

The above compound 3 may be present in an enol-keto form of tautomer.

[Compound 3]

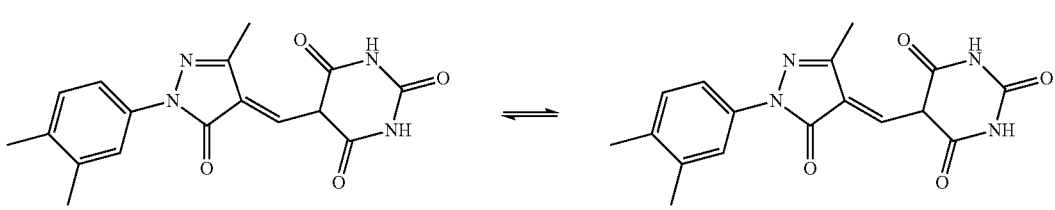

The RNase activity inhibitory compound according to the present invention may particularly include compounds represented by the following formulae.

[Compound 1]

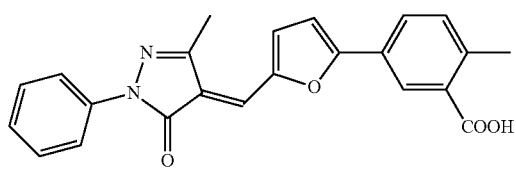

[Compound 2]

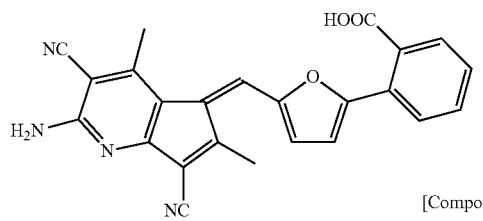

[Compound 3]

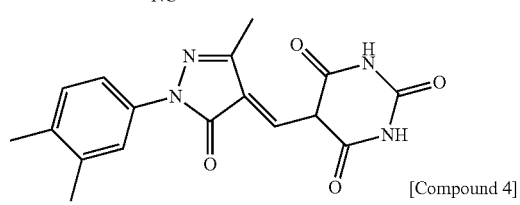

[Compound 4]

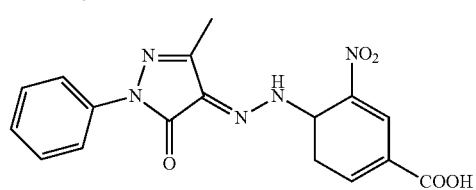

The RNase is preferably an endo-ribonuclease including, in particular, RNase A, RNAse H, RNAse I, RNase III, RNase L, RNase P, RNase PhyM, RNase T1, RNase T2, RNase U2, RNase V1 and RNase V.

The RNA applied to the present invention may include ribosomal RNAs, messenger RNAs, transfer RNAs, etc., and preferable examples thereof, that is, RNases having activity inhibited by the inventive RNase activity inhibitory compound may include: RNase A, RNase H, RNase I, RNase III, RNase L, RNase P, RNase PhyM, RNase T1, RNase T2, RNase U2, RNase V1, RNase V, etc.; and other than the foregoing, exo-RNases including PNPase(Polynucleotide Phosphorylase), RNase PH, RNase II, RNase R, RNase D, RNase T, Oligoribonuclease, Exoribonuclease I, Exoribonuclease II, or so forth.

In order to easily use the RNase activity inhibitory compound according to the present invention, the compound may be dissolved in at least one selected from a group consisting of water, DMF, DMSO, lower alcohols having 1 to 5 carbon atoms (for example, methylalcohol, ethylalcohol, isopropylalcohol, butanol, etc.) or mixed solvents thereof.

The RNA may include samples such as animal tissue, plant tissue, microorganisms, blood, plasma, serum, culture cells, and products transfected from the above samples using recombinant genes.

The present invention may provide a container for storage of RNAs, which includes the RNase activity inhibitory compound of the present invention, in order to stably retain RNAs liable to be degraded due to exposure to the RNase during storage thereof. In this regard, the RNA sample storage container may also include the compound for inhibiting the activity of the RNase applied to an inner wall of the container.

Advantageous Effects

The RNase activity inhibitory compound according to the present invention may effectively prevent RNAs from being degraded by influence of an endo-RNase and an exo-RNase during storage of a sample collected to extract RNAs. In addition, a container for storage of a biological sample, which was processed using the RNase activity inhibitory compound, may efficiently inhibit RNA degradation occurring in storage and transportation of the biological sample, thereby enabling effective application thereof in diagnosis and/or experimental work carried out in hospitals, schools, laboratories, and the like.

DESCRIPTION OF DRAWINGS

The above and other objects, features and advantages of the present invention will become apparent from the following description of preferred embodiments given in conjunction with the accompanying drawings, in which.

BEST MODE

Figure 1:
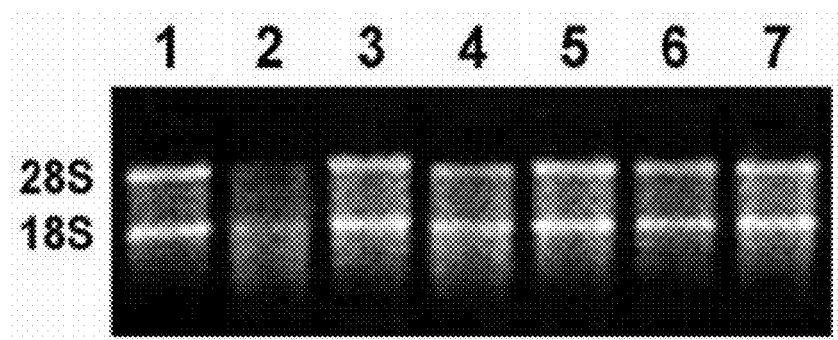
FIG. 1 is a photograph show results of electrophoresis using agarose gel and separation of RNAs treated using an RNase activity inhibitory compound, compared to those not treated by the above compound, after extracting both the RNAs from a culture cell and treated using a human serum.

Hereinafter, preferred embodiments of the present invention will be described in more detail.

A preparation method of the present invention will be proposed for illustrative purpose in the following examples, however, the present invention is not particularly restricted to the foregoing method and, instead, may be easily and obviously understood by those skilled in the related art, to which the present invention pertains.

Furthermore, scientific and technological terminologies used herein include the meanings commonly understood in the related art by those having ordinary knowledge in the related art, except where otherwise noted. When technical configurations known in the related art are considered to make obscure contents of the present invention, the detailed description thereof will be omitted.

The compounds according to the present invention described herein are obtainable from compound libraries of Inter-Bio Screen (United States), Specs (The Netherlands), Asinex Ltd. (Russia), etc.

Example 1

Influence of Treatment Using RNase Activity Inhibitory Compound Upon Activity of RNase (1) Preparation of RNase Activity Inhibitory Composition The compounds for inhibiting activity of an RNase used in the present invention were purchased from Specs in The Netherlands and employed. Features of respective compounds are listed in Table 1.

TABLE 1

|  | Compound 1 | Compound 2 | Compound 3 | Compound 4 |
|---|---|---|---|---|
| Molecular weight | 386.4 | 408.4 | 310.3 | 367.3 |
| Formula | $C_{23}H_{18}N_2O_4$ | $C_{24}H_{26}N_4O_3$ | $C_{17}H_{15}N_2O_2$ | $C_{17}H_{13}N_3O_3$ |

After taking 2 mg of each compound described above, the compound was dissolved in 1 ml of DMSO (Dimethyl sulfoxide, F.W 78.13, Sigma, D2650) and then stored in a dark bottle.

(2) Preparation of RNase

For normal people, about 120 units of RNases are present in 1 ml of a human serum and such RNases generally have a very stable structure even at room temperature, therefore, well known to be useable in various experiments (K. K. Reddi et. al., PNAS, 73:2308-2310 (1976)).

For screening materials having high activity inhibition to a variety of endo-RNases present in the human serum, Pooled Human Normal Serum (Cat. No. IPLA-5, Lot No. IR07-010) were purchased from Innovative Research in the United States and used for experiments after dilution 10 times using sterile PBS (Phosphate Buffered Saline) buffer, for experiments.

(3) Confirmation of Inhibition Status of Activity of RNase

Total RNA was extracted from HeLa cells (HeLa, $1 \times 10^6$ cells/rxn) using AccuZol™ Total RNA Extraction Reagent (K-3090) of Bioneer Co., according to instructions enclosed therein.

Briefly, processes of extracting total RNA will be described below. First, 1 ml of AccuZol™ Total RNA Extraction Reagent was added to the collected HeLa cells ($1 \times 10^6$ cells) and sufficiently mixed. Then, 200 ul of chloroform was added thereto and mixed for 15 seconds. After leaving the prepared solution on ice for 15 minutes, centrifugation was conducted at 12,000 rpm and 4° C. for 15 minutes. After centrifugation, a supernatant only was gently decanted from the tube to a new tube and the same amount of isopropyl alcohol was added thereto and sufficiently mixed. After leaving the treated mixture at −20° C. for 10 minutes, centrifugation was conducted at 12,000 rpm and 4° C. for 10 minutes, thus enabling settlement of total RNA only. Using 1 ml of 80% ethyl alcohol, organic solvent residue or salt on the inner wall of the tube was washed out, followed by centrifugation at 12,000 rpm and 4° C. for 10 minutes, thus enabling settlement of pure total RNA only at the bottom of the tube. The tube was dried at room temperature to completely remove ethyl alcohol residue. Further, in order to prevent contamination of RNases, the total RNA was dissolved in double-distilled and deionized water (pure water), which was treated using DEPC (Diethylpyrocarbonate, Sigma, D5758), and stored at −80° C.

Figure 2:
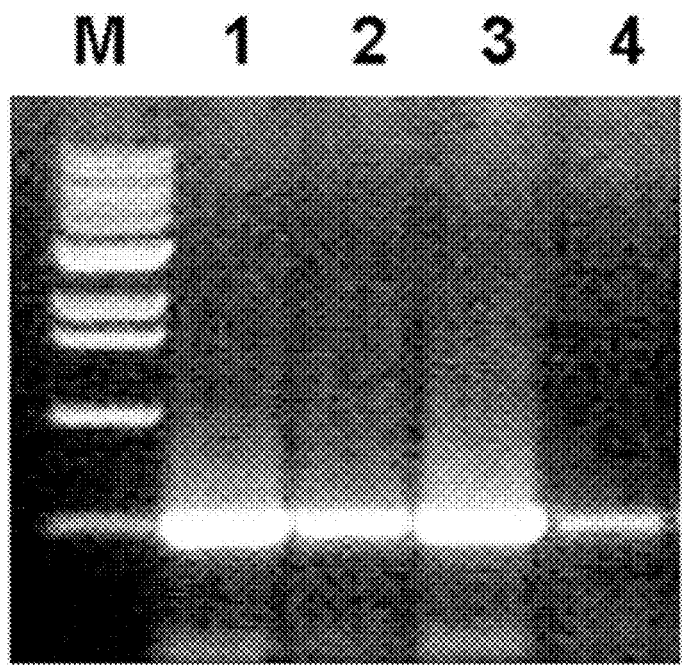
FIG. 2 is a photograph showing results of electrophoresis using agarose gel of a reaction product obtained by reverse-transcription polymerase chain reaction using RNA treated with the RNase activity inhibitory compound of the present invention.
Figure 3:
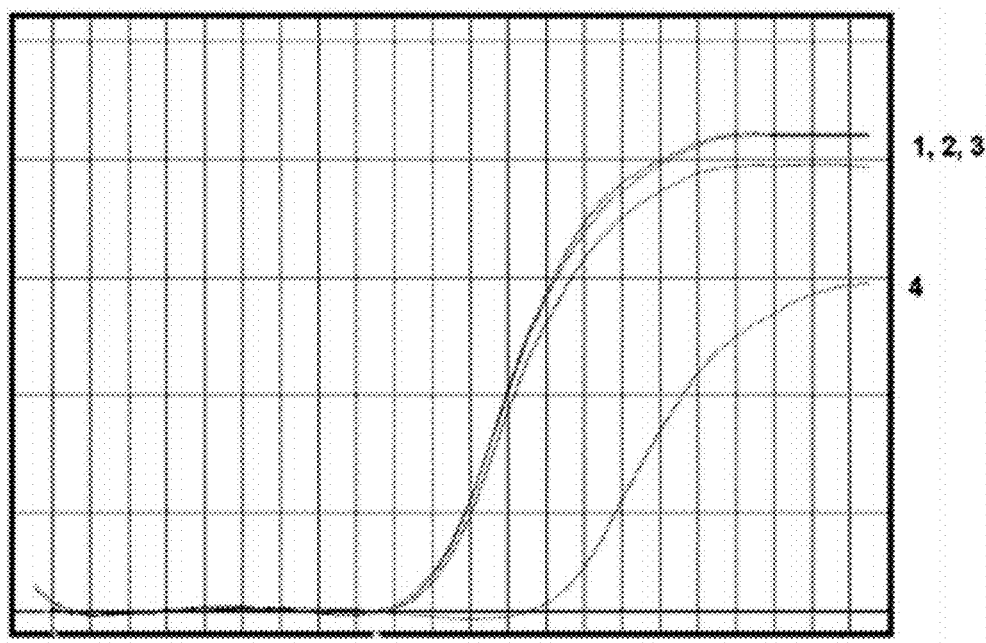
FIG. 3 illustrates results of real-time reverse-transcription polymerase chain reaction executed using RNA treated with the RNase activity inhibitory compound of the present invention.

The extracted total RNA was subjected to measurement of absorbance using a Pico-drop apparatus and determination of the total yield and purity based on the measured result. After placing 5 µg of a human total RNA in a 1.5 ml tube, 5 µl (10 µg) of each of the four types of materials prepared above was added to the tube and sufficiently mixed. After placing 5 µl of the human serum prepared above in the tube, it was subjected to culturing in an incubator at 37° C. for 5 minutes. After completing the culturing, the human serum was purified immediately using AccuZol™ Total RNA Extraction Reagent (Bioneer, K-3090) and the RNA was finally dissolved in the sterile water treated using 10 µl of DEPC (Diethyl pyrocarbonate, Sigma, D5758). Through electrophoresis using agarose gel for RNA, degradation status by the RNA in the human serum was observed (FIG. 2).

As a result, a control group without the human serum treatment (Lane 1) showed complete preservation of RNAs even after a reaction was carried out at 37° C. for 5 minutes. Another control group without treatment using an RNase activity inhibitory material (Lane 2), even though having been treated using the human serum, showed complete degradation of RNAs. Further, another control group treated using a commercially available RNase activity inhibitory material (Lane 3) exhibited RNAs well preserved without degradation thereof. On the other hand, it can be seen that all test samples treated using RNase activity inhibitory materials selected in the present invention (Lanes 4, 5, 6 and 7) have total RNAs completely preserved without degradation thereof.

Example 2

Influence of Treatment Using RNase Activity Inhibitory Compound Upon Other Experiments If treatment using the RNase activity inhibitory compound influences molecular biological experiments, the compound cannot be employed although it exhibits superior RNase inhibitory effects. Accordingly, in order to investigate such side-effects, RNAs treated with the RNA inhibitory material are used to conduct real-time reverse transcription-polymerase chain reaction (real-time RT-PCR) as well as RT-PCR.

(1) Confirmation of Inhibition Status of RT-PCR

Using an RNA treated using an RNase activity inhibitory compound as a template strand, RT-PCR was carried out using a primer set capable of amplifying a glyceraldehyde-3-phosphate dehydrogenase (GAPDH) gene site in the human, as well as AccuPowerRT-PCR premix (Bioneer, K-2055). Conditions for RT-PCR are as follows: a single strand, cDNA (complementary DNA) was synthesized through a reaction at 42° C. for 60 minutes, followed by inactivation of a reverse-transcriptase at 94° C. for 5 minutes and then PCR. Such PCR was performed by repeating a series of processes 30 times, including: DNA denaturation at 94° C. for 20 seconds; annealing of each primer to a target site at 60° C. for 20 seconds; and preparation of a double-strand DNA through extension of a complementary strand at 72° C. for 30 seconds. A size of a reaction product of RT-PCR was confirmed through 1% agarose gel electrophoresis (FIG. 2).

As a result, only one (Lane 4) among the selected four compounds for inhibiting RNases showed inhibitory effects against RT-PCR, although such effects are not remarkable. It was found that the remaining three compounds never have RT-PCR inhibitory effects (Lane 1, 2, 3).

(2) Confirmation of Inhibition Status of Real-Time RT-PCR

Using GAPDH gene site in the human as a target, a primer set and a probe having FAM at 5'-end as well as BHQ at 3'-end were prepared. Then, a real-time RT-PCR was executed using the RNA treated with an RNase inhibitory material as a template strand. The RT-PCR was performed by synthesizing a single strand, cDNA at 45° C. for 15 minutes and inactivating a reverse-transcriptase at 94° C. for 5 minutes. Such a real-time RT-PCR was performed by repeating a series of processes 45 times, including: DNA denaturation at 94° C. for 5 seconds; and preparation of a double-strand DNA at 55° C. for 5 seconds through annealing of each primer to a target site and extension of a complementary strand. As an apparatus for the real-time RT-PCR, ExiCycler™ 96 Quantitative Thermal Block manufactured by Bioneer Co., was used. Moreover, M-MLV Reverse Transcriptase (E-3121) and Top DNA Polymerase (E-3100) were employed as a reverse-transcriptase and a polymerase, respectively.

As a result, only one (Lane 4) among the selected four compounds for inhibiting RNases showed inhibitory effects against the real-time RT-PCR. It was found that the remaining three compounds never have RT-PCR inhibitory effects (Lane 1, 2, 3).

The invention claimed is:

1. A compound for inhibiting activity of an RNase represented by the following Formula 1 or 2:

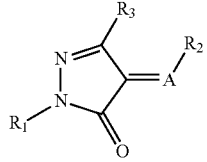

[Formula 1]

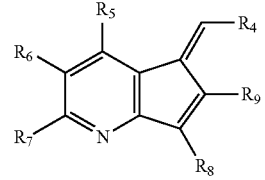

[Formula 2]

wherein, in Formula 1 or 2, A is CH or N; $R_1$ is

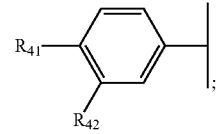

$R_{41}$ or $R_{42}$ is each independently hydrogen, a linear or branched ($C_1$-$C_7$)alkyl, provided that in the case where $R_2$ or $R_4$ is

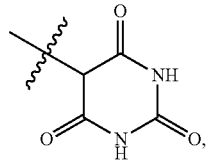 [SMILES: *C1C(=O)NC(=O)NC1=O]

$R_{41}$ is not hydrogen; $R_2$ or $R_4$ is each independently

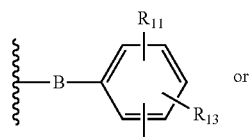

or

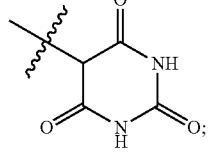

$R_3$ is a linear or branched $(C_1-C_7)$alkyl; B in the substitute $R_2$ or $R_4$ is

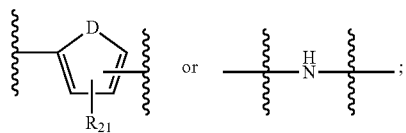

$R_5$ to $R_9$ are each independently hydrogen, linear or branched $(C_1-C_7)$alkyl, carboxylic acid, halogen atoms, cyano, amino, mono- or di$(C_1-C_7)$alkylamino, guanidine, urea or formyl; $R_{11}$, $R_{12}$ or $R_{13}$ is each independently hydrogen, linear or branched $(C_1-C_7)$alkyl, $(C_3-C_7)$cycloalkyl, $(C_3-C_{10})$cycloalkyl$(C_1-C_7)$alkyl, carboxylic acid, halogen atoms, cyano, nitro, amino, mono- or di$(C_1-C_7)$alkylamino, $(C_3-C_7)$cycloalkylamino, morpholine, morpholine oxide, piperazine, piperazine oxide, guanidine, urea, benzyl, benzyloxy or formyl; $R_{21}$ is hydrogen or linear or branched $(C_1-C_7)$alkyl; D is O, S or $-NR_{22}$; $R_{22}$ is hydrogen or $(C_1-C_7)$alkyl.

2. The compound of claim 1, wherein the compound is selected from compounds represented by any one of the following Formulae 3 to 6:

[Formula 3]

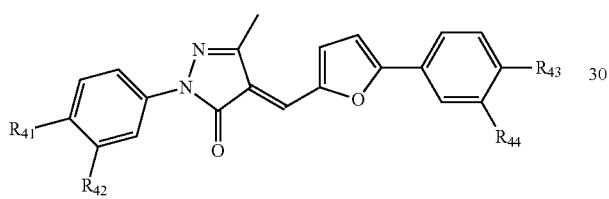

[Formula 4]

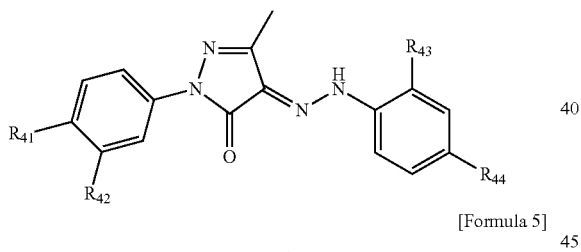

[Formula 5]

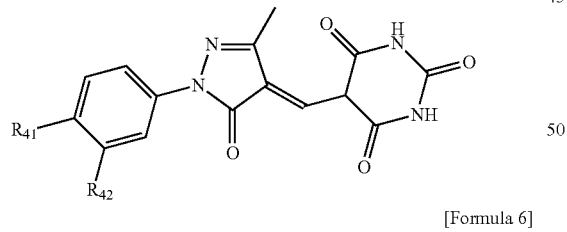

[Formula 6]

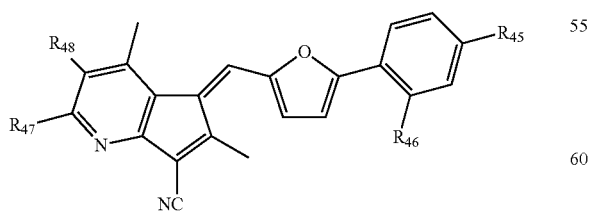

wherein, in Formulae 3 to 6, $R_{41}$ or $R_{42}$ is each independently hydrogen, methyl, ethyl, n-propyl or i-propyl, provided that in Formula 5, $R_{41}$ is not hydrogen; $R_{43}$ or $R_{44}$ is each independently hydrogen, methy, ethyl, n-propyl, i-propyl, carboxylic acid or nitro; $R_{45}$ or $R_{46}$ is each independently hydrogen, methyl, ethyl, n-propyl, i-propyl or carboxylic acid; $R_{47}$ or $R_{48}$ is each independently hydrogen, methyl, ethyl, cyano or amino.

3. The compound of claim 2, wherein the compound is selected from compounds represented by the following formulae:

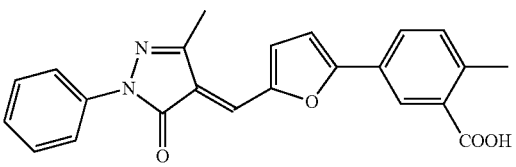

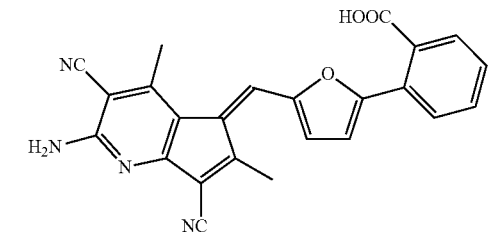

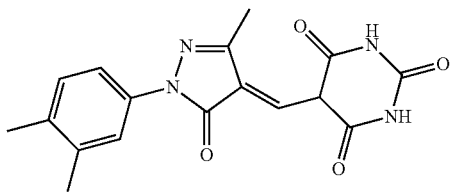

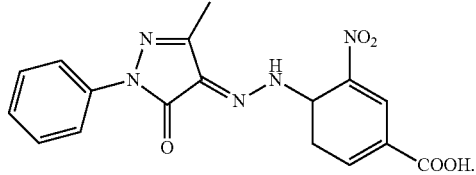

4. A composition for inhibiting activity of an RNase comprising the compound of claim 1 dissolved in a solvent.

5. The composition of claim 4, wherein the solvent is at least one selected from water, DMF, DMSO, (C1-C5) lower alcohol or mixed solvents thereof.

6. A method of inhibiting endo-RNase activity comprising, applying the compound of claim 1 to a sample selected from the group consisting of animal tissue, plant tissue, microorganisms, blood, plasma, serum, culture cells, and products transfected from the foregoing samples using recombinant genes.

7. An RNA sample storage container comprising an inner wall, wherein the RNase activity inhibitory compound of claim 1 is applied to the inner wall.

8. The container of claim 7, wherein the RNase activity inhibitory compound is present in a freeze-dried form.